United States Patent [19]

Lia et al.

[11] Patent Number: 4,700,693

[45] Date of Patent: Oct. 20, 1987

[54] ENDOSCOPE STEERING SECTION

[75] Inventors: Raymond A. Lia; Robert L. Vivenzio, both of Auburn, N.Y.

[73] Assignee: Welch Allyn, Inc., Skaneateles Falls, N.Y.

[21] Appl. No.: 806,667

[22] Filed: Dec. 9, 1985

[51] Int. Cl.⁴ ............................................... A61B 1/00
[52] U.S. Cl. ......................................................... 128/4
[58] Field of Search ......................................... 128/4–8; 73/151; 464/51, 81, 106, 179, 906

[56] References Cited

U.S. PATENT DOCUMENTS

| | | | |
|---|---|---|---|
| 1,817,000 | 8/1931 | Granville | 464/179 |
| 2,286,182 | 6/1942 | Amberg | 464/906 |
| 3,060,972 | 10/1962 | Sheldon | 128/4 |
| 3,106,077 | 10/1963 | Sharp | 464/906 |
| 3,190,286 | 6/1965 | Stokes | 128/6 |
| 3,572,325 | 3/1971 | Bazell et al. | 128/6 |
| 3,788,304 | 1/1974 | Takahashi | 128/6 |
| 4,108,211 | 8/1978 | Tanaka | 128/4 |

FOREIGN PATENT DOCUMENTS 2143920  2/1985  United Kingdom ..................... 128/4

Primary Examiner—Kyle L. Howell
Assistant Examiner—Max F. Hindenburg
Attorney, Agent, or Firm—Bruns and Wall

[57] ABSTRACT

A steering section for an endoscope or borescope employs a plurality of steering cables passing through peripheral bores in axially aligned flat washers. Spacer beads are strung on the cables between the washers to define hinges for the bending of the steering section. Pairs of hemispherical beads are employed for this purpose, and are disposed nose-to-nose, that is, with their spherical surfaces rocking on one another. Tuning spacer beads are provided in selected inter-washer spaces to limit the bending of the tuning section in one direction. To achieve the smallest possible dimension, the washers can be formed with an oval or elongated passageway.

15 Claims, 8 Drawing Figures

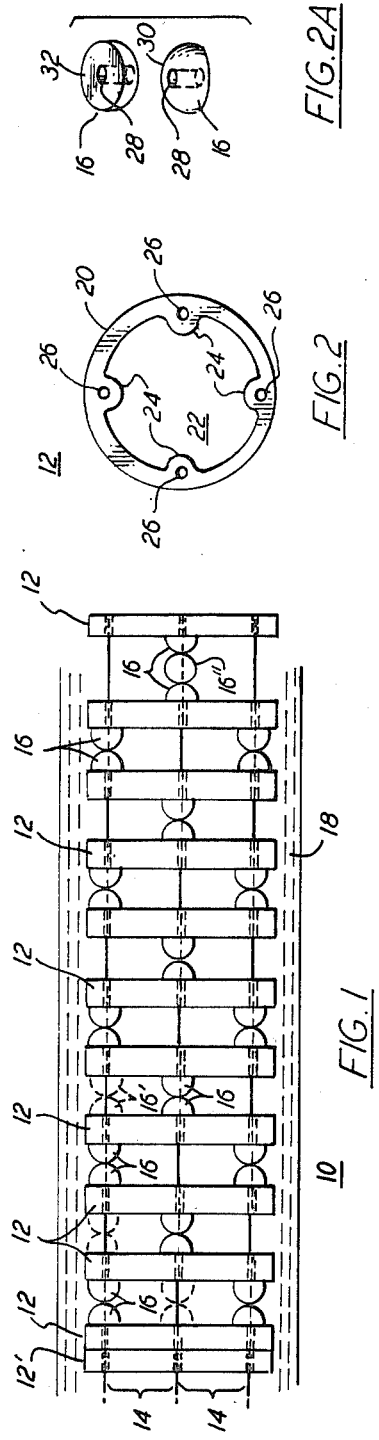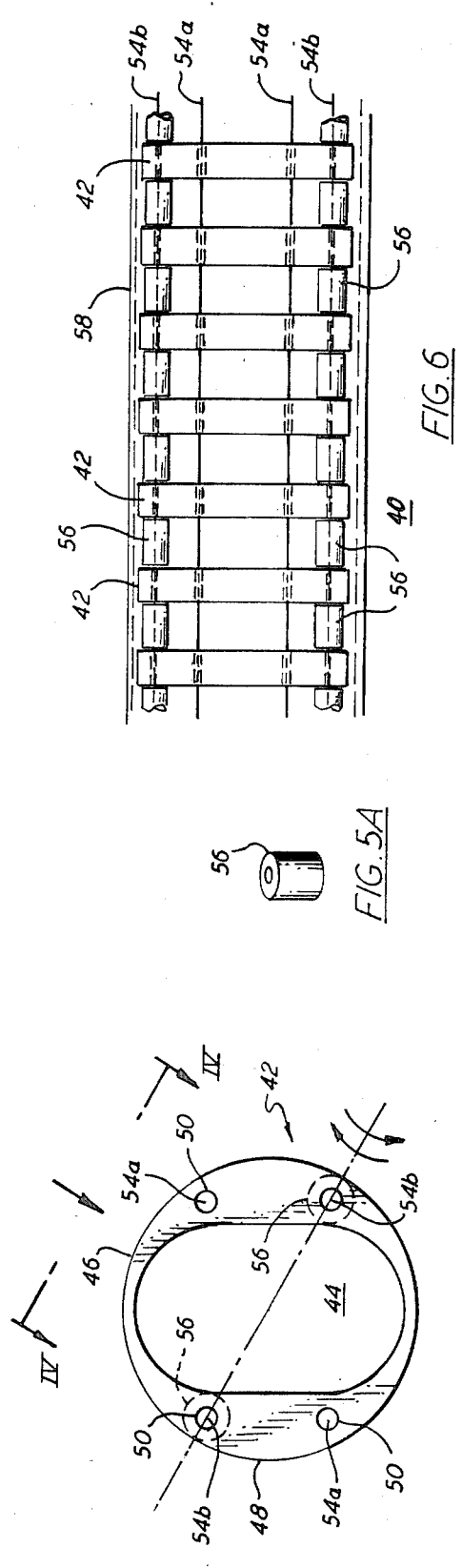

ENDOSCOPE STEERING SECTION

BACKGROUND OF THE INVENTION

This invention relates to a controllably bendable tube assembly, especially a hollow steering section of a borescope or endoscope.

An endoscope is generally characterized as an elongated flexible tube with a viewing head in its distal or forward end, and a control housing at its proximal end for controlling or steering the distal end. In such an endoscope, a bendable tube section is provided at the distal end adjacent to the viewing head. One or two pairs of control cables extend through the bendable tube section and the remainder of the flexible tube and connect with a steering control in the control section. One, or both pairs of these cables are displaced in order to bend the bendable section to facilitate the inspection of an object.

An endoscope is typically inserted into the cavity of a patient in order to visually investigate the tissues within the cavity. For example, an endoscope can be inserted into the colon, stomach, or into the lung of a patient. Because the esophagus, bronchii and the colon are narrow, tortuous passageways, the steering section must be bent rather precisely, and as close to the head as possible, in order to obtain the necessary penetration without damaging the patient's tissues. It is most desirable that the bending take place as close to the viewing head as the steering section is bent in a full arch or in a partial arch, and it is also most desirable that the play or slop in the cable be kept to a minimum.

A borescope is a similar device, but intended for visual inspection of a mechanical device, such as a jet engine or turbine, where it would be difficult or impossible to examine the device's internal elements. The borescope needs to be insertable into narrow tortuous passageways, and must observe similar steering and bending considerations.

A number of types of steering mechanisms are known. For example, helically coiled strips are employed in endoscopes or borescopes as descibed in U.S. Pat. Nos. 3,610,231 and 3,739,770. Steering sections having thin walled cylindrical segments or bands that are joined by means of pins or bifurcations, or other similar articulations such that the segments are rockable on one another, are described in U.S. Pat. Nos. 3,583,393; 3,669,098; 3,799,151; and 4,347,837. A previously-proposed endoscope that had a provision to control the degree of bending is described in U.S. Pat. No. 3,557,780. In that endoscope, the steering section was formed of two flexure portions, and had two sets of control wires. Stays or flexible backbone members of various lengths were employed so that the degree of curving and the location of the curvature on the steering portion could be controlled.

In the endoscope described in the U.S. Pat. No. 3,799,151, cylindrical segments were articulated in one plane or in another plane as required to select the amount and direction of bending of the endoscope steering portion.

From a consideration of the foregoing, it becomes apparent that the steering mechanisms for these previously-proposed endoscopes are rather elaborate structures, with many parts that can fail and which are relatively expensive to produce. Also, in the case of steering sections which are bendable in two planes, it has been necessary to provide the cables with a significant amount of slop or play, because the steering sections bend at discrete points, and not in a perfectly smooth curve.

OBJECTS AND SUMMARY OF THE INVENTION

Accordingly, it is an object of this invention to provide a cable-bendable steering section for a borescope or endoscope which avoids the drawbacks of the prior art.

It is another object of this invention to provide a cable-bendable steering section that avoids undesirable play or slack in the steering cable.

It is a further object of this invention to provide a steering section that avoids slapping or clicking of the parts of the steering mechanism.

It is a still further object of this invention to provide a cable-bendable steering section that is tuned to turn at a predetermined arc.

It is a yet further object of this invention to provide a cable-bendable steering section for a borescope or endoscope wherein the turning is limited in one direction, and preferably wherein the limited turning is concentrated toward the distal end of the steering section.

It is yet another object of this invention to provide a cable-bendable steering section for a borescope or endoscope of the smallest possible diameter, wherein the necessary cables and electrical or optical leads can be adequately accommodated therewithin.

As aforesaid, the invention resides in a steerable endoscope or borescope of the type having a viewing head and a cable-bendable steering section disposed proximally of the viewing head. The steering section has a flexible sheath, a plurality of washers, each having a central passage and a plurality of peripheral bores therethrough, pairs of which are disposed generally diametrically opposite of each other, and a plurality of steering cables passing through respective axially aligned ones of the peripheral bores of the washers. Spacing structure is disposed at the location of at least certain ones of the peripheral bores associated with predetermined ones of the cables and this structure defines bending locations for the steering section such that the displacement of certain pairs of the steering cables result in the bending of the steering section in one plane or another. The invention contains the improvement in which the washers are flat washers and the spacer structure includes pairs of hemispherical beads that are disposed in nose-to-nose fashion over the predetermined cables between successive ones of the washers, with the beads having spherical surfaces facing one another and flat surfaces facing their associated washers. Preferably, the beads are molded of a self-lubricating synthetic resin material, which can be a blend of nylon, carbon and Teflon. The ratio of the washer thickness to the separation between washers should be about 0.5 to 2.5.

According to this invention, the cable-bendable steering section can be tuned so that it is limited in its bending and in one plane in one direction, and not limited in the other direction. In one example of the tuned steering section, the spacer structure is generally staggered, so that the spacer beads disposed at the location of one pair of peripheral bores are situated in alternating ones of the inter-washer spaces, while the spacer beads associated with the other pair of peripheral bores are situated in the remaining spaces. To effect tuning, tuning spacer beads are disposed at the location of one only of the other pair of bores in the alternating inter-washer spaces to limit the bending in the direction of the tuning spacer beads, but not in the direction away from the tuning spacer beads. The tuning spacer beads are preferably disposed towards the proximal end of the steering section, so that the limited bending is concentrated towards the distal end thereof, i.e. on the portion towards the viewing head.

In order to make the borescope or endoscope as small as possible in diameter, the flat washer can be constructed of a generally circular outer shape, but with a central passage that is generally oval in shape, such that the washers have side portions that are thicker in the direction across the oval passage. The washer has pairs of bores disposed to each side of the oval passage. The two bores on each side portion are then angularly separated by less than a right angle.

Most favorably, the washers are formed of beryllium copper or aluminum bronze.

The foregoing and many other objects, features, and advantages of this invention will become apparent from the ensuing detailed description of preferred embodiments thereof, which description is to be considered in connection with the accompanying drawing.

BRIEF DESCRIPTION OF THE DRAWING

FIG. 1 is a sectional view of a steering section of an endoscope or borescope according to a first embodiment of this invention.

FIG. 2 is a plan view of a washer of the first embodiment.

FIG. 2A is a perspective view of spacer beads employed in the first embodiment.

FIG. 5 is a plan view of a washer employed in a second embodiment of this invention.

FIG. 5A is a perspective view of a spacer bead employed in the second embodiment FIG. 6 is a section view of the steering section of an endoscope or borescope of the second embodiment.

DETAILED DESCRIPTION OF THE PREFERRED EMBODIMENTS

Figure 3:
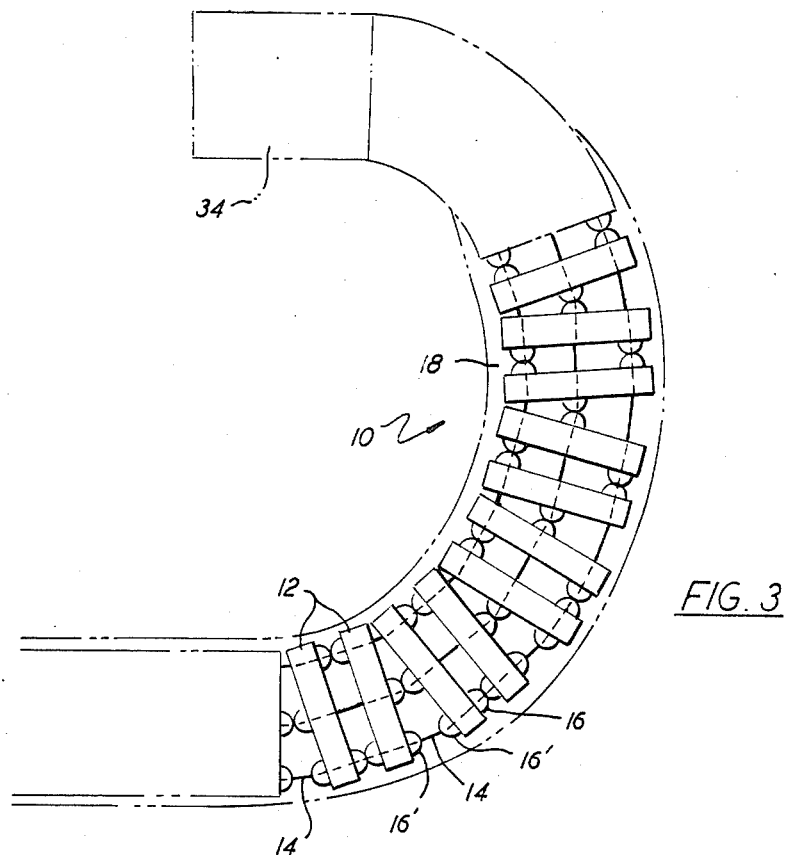
FIGS. 3 and 4 are sectional views for explaining the tuning feature of the, first embodiment.

Referring to the drawings, and initially to FIG. 1 thereof, a generally cylindrical steering section 10 of an endoscope or borescope is disposed with a proximal end (to the left in the drawing) connected to an elongated flexible tube, and with a distal end (to the right in the drawing) on which there is mounted a video or fiber optics type viewing head.

The steering section 10 is formed of a stack of washers 12, one of which is shown in plan in FIG. 2. With these washers 12 are associated two pairs of steering cables 14, which are preferably twisted strand stainless steel cables. Hemispherical spacer beads 16 (show in perspective in FIG. 2A) are disposed over the cables 14 in the spaces between the washers 12, and this assembly is covered with a flexible sheath 18.

The washer 12 as shown in FIG. 2 can favorably be composed of aluminum bronze or beryllium copper. If composed of the latter alloy, the washers 12 can be easily photo etched from a sheet thereof.

The washers 12 are basically in the form of a circular ring 20, here are about 13 millimeters diameter and about 1 millimeter thick. The washer 12 has a generally cruciform (cross-shaped) central passage 22 which is defined between inwardly directed lobes 24 spaced at 90 degree intervals on the ring 20. Peripheral through-bores 26 penetrate the lobes 24. The stack of washers 12 has respective bores aligned in registry with one another.

Figure 4:
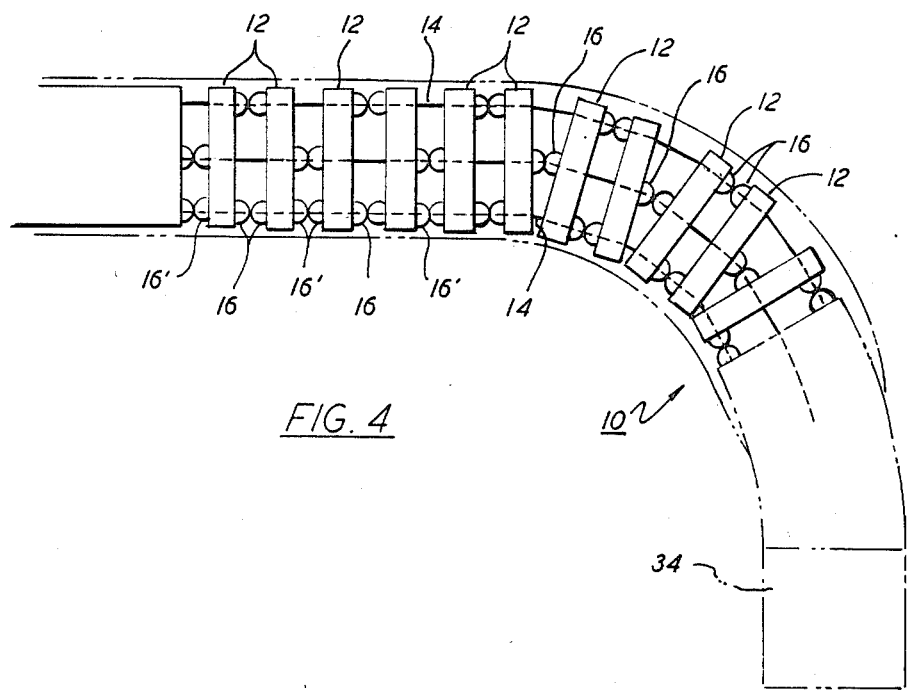

The hemispherical spacer beads 16 each have an axial passage 28, a spherical surface 30, and a flat surface 32. The spherical surfaces of the two beads 16 between any particular pair of washers 12 are disposed in a nose-to-nose configuration, that is, with the spherical surfaces 30 facing one another. The flat surfaces 32 are disposed against the respective lobes 24 of the associated washers. Pairs of these washers 16 are disposed in alternate inter-washer spaces on each of the steering cables 14, i.e., at the top and bottom of the drawing, and in the remaining spaces over the other two cables 14, that is, the front and back (obscured) in the drawing. The hemispherical beads 16 associated with the top and bottom cables 14 provide pivots to define hinge lines for bending the steering section in a sideways direction, that is, into and out of the drawing in FIG. 1, while the beads 16 associated with the remaining cables 14 define hinge lines for the bending of the steering section 10 in the direction upward and downward in the drawing. The cables 14 pass through the bores 26 and the bead passages 28 and slide relative to the beads 16 and washers 12. These cables 14 are anchored to a point in the viewing head, and their displacement causes flexion of the steering section to bend the same in an arch, generally as shown in FIGS. 3 and 4, the general manner of which is well known.

The spherical surfaces 30 of the facing spacer beads 16 rock with respect to one another to form smooth bending points, while the flat surfaces 32 of the beads 16 seat against the lobes 24 of the washers 12. As a result of this structure, the amount of slop or play in the steering cables 14, which would otherwise be required for steerabililty in two planes, can be minimized or substantially eliminated. This permits better precision in bending the steering section 10. Also, because of this structure, including these hemispherical beads 16, the steering section 10 does not snap or click as the cables 14 are displaced, thus eliminating further inaccuracies in the control over turning of the steering section 10.

The beads 16 are favorably molded of a composite of nylon, carbon, and Teflon (tetrafluoroethelene) to be both durable and self-lubricating. The steering section, including the cables 14, the washers 12, and the beads 16 are "self lapping" because the material of the cable 14 is harder than that of the washer 12, and both are harder than the beads 16. Over time, the repeated displacement of the cable 14 works channels in the axial passage 28 of the spacer beads 16, thus, the cable 14 cuts its own seat in the beads 16, prolonging the life of the cables 14 and the washers 12.

As mentioned previously, the beads 16 are disposed such that the displacement of one of the pairs of cables 16 associated with diametrically disposed bores 26 of the washers 12 will bend the steering section into one plane, while displacement of the steering cables 14 associated with the other pair of diametrically opposed bores 26 will bend the steering section 10 in a plane at 90 degrees to the first mentioned plane.

As aforesaid, the arcuate bending of the steering section 10 begins from the rearward or proximal end of the steering section 10 as the cables 14 are displaced, and then continues forward towards the distal or viewing-head end thereof. Accordingly, if it is desired that small amounts of bending of the steering section 10 be concentrated toward the viewing-head or distal end of the steering section 10, tuning means can be provided within the steering section 10.

In this embodiment, tuning spacer beads 16', shown in ghost line in FIG. 1, are disposed over one cable of one pair of cables 14 in selected ones of the remaining spaces between washers 12. Here, the spacer beads 16' are disposed in the spaces towards the proximal or rearward end of the steering section 10. The effect of these tuning spacer beads 16' can be understood from a comparison of FIGS. 3 and 4. As shown in FIG. 1, a washer 12' at the proximal end can be placed directly against the next successive washer 12, without intervening spacer beads 16. Also, a different tuning characteristic can be achieved by placing a spherical spacer bead 16'' between the facing hemispherical beads 16 at selected locations.

In FIGS. 3 and 4, which illustrate the embodiment of FIG. 1 and in which similar elements are identified with the same reference characters as in FIG. 1, the tuning spacer beads 16' are disposed towards the proximal end of the steering section 10, i.e., away from a distal viewing head 34, and on the lower most one of the cables 14. If it is desired to turn the steering section 10 over a full arc, the upper one of the cables 14 is drawn out, thus collapsing the spaces between the washers 12 over the entire inside of the curve as shown. However, if it is desired to bend the steering section 10 over a lesser arc, the lower one of the cables 14 is drawn out, and the tuning beads 16 prevent the collapse of the inter-washer spaces that are disposed towards the proximal end of the turning section 10. Accordingly, the turning or bending is concentrated towards the viewing head 34.

This arrangement ensures that for small angles of bending, the bending is concentrated toward the viewing head 34, despite the tendency of the washer and cable bending mechanism to begin its bending from the proximal end. That is, the blocking action of the tuning beads 16' tunes the bendability to the desired portion of the bending steering section 10, so that the desired arc can be achieved. The placement of the tuning beads 16' can be selected different for each of the four cables 14, such that different degrees of bending are achieved in each of four bending directions.

Another embodiment of this invention is shown with respect to FIGS. 5, 5A and 6. In the second embodiment, an off-axis arrangement of cables is employed in a steering section 40 of a small-diameter borescope or endoscope. The structure of this second embodiment achieves as small as possible an outside diameter, yet has provision for sufficient passageway clearance to accomodate the necessary fiber optics, electrical cables, air, water, and sampling channels required for the endoscope or borescope device.

The steering section 40 is formed of a plurality of washers 42 which are shown in plan in FIG. 5 and as stacked together in FIG. 6.

Each washer is about 5 millimeters in diameter, and has an oval passage 44 therein of about 4.5 millimeters in length, and 2.8 millimeters in width. This passage 44 can be of an eliptical or "racetrack" shape. This washer 42 is in the form of a ring 46 with wide portions 48 in the direction across the oval passage 44, and with two pairs of peripheral bores 50 disposed in the wide portions 48. The bores 50 of each pair are disposed diametrically opposite one another. Because of the requirement for an oval or elongated passage 44, the adjacent bores 50 in each of the wide portions 48 are separated by less than 90 degrees, in this embodiment, by about 60 degrees.

A pair of steering cables 54a, 54a is disposed through the bores of the opposite-disposed pairs of bores 50, while a pair of fixed cables 54b, 54b is disposed through the other pair of bores 50. Spacers 56 (shown in FIG. 5A) are disposed over the cables 54b in the spaces between the washers 42. These spacers 56 are preferably cylindrical beads of copper or bronze, are provided with axial bores, and are about 0.020 inches (0.5 mm) in height and 0.020 (0.5 mm) inches in diameter. A sheath 58 covers the bending section 40.

The spacers 56 define bending lines as shown in chain in FIG. 5, so that when the cables 54a are manipulated, the washers 42 rock in the direction normal to those bending lines in the desired arc.

The dimensions of the washers 12 and 42 of these embodiments and of the spacer beads 16 and 56 hereof are selected so that the proper amount of bending or arc is achieved in the steering sections 10 and 40, and so that the washers 12 and 42 will provide a sufficient amount of protection for the cable leads, and channels that are disposed on their interiors. It is preferred that the thickness of the washers 12, 42 to the separation achieved by the spacers 56 and 16 be in a range of about 1.5 to 2.5.

Although not shown in FIGS. 5, 5A, and 6, tuning spacers can also be employed in the second embodiment.

It should be apparent that the spacers 16 and 16' of the first embodiment can be staggered in the fashion as illustrated in FIG. 1, or can be set out in any of many possible alternate fashions, for example, open blocked-blocked, or open-open-blocked, so as to achieve a particular desired bending characteristic for the steering section 10.

Also, while the washers 12 and 42 of these two embodiments are flat, in other possible embodiments the washers could be arcuate or saddle-shaped, depending on the particular application.

While a detailed description is given of the preferred embodiment of this invention, it should be apparent that many modifications and variations thereof would present themselves to those of skill in the art without departure from the scope and spirit of this invention, as defined in the appended claims.

We claim:

1. In a steerable endoscope or borescope of the type having a viewing head, a cable-bendable steering section proximally of said viewing head including a flexible sheath, a plurality of axially aligned washers each having a central passage and a plurality of peripheral bores therethrough, pairs of which are generally diametrically disposed, a plurality of steering cables passing through respective axially aligned peripheral bores of said washers, and spacer means disposed at the locations of at least certain peripheral bores associated with predetermined cables and serving to define bending locations for said steering section such that displacement of certain steering cables results in the bending of said steering section; the improvement wherein said washers are flat planar washers and said spacer means include pairs of hemispherical beads disposed over said predetermined cables between successive ones of said washers, said beads having spherical surfaces in rocking contact against one another and flat surfaces facing their associated washers.

2. The steerable endoscope or borescope of claim 1 wherein said beads are molded of a self-lubricating material.

3. The steerable endoscope or borescope of claim 2 wherein said material is a blend of nylon, carbon, and tetrafluoroethelene.

4. The steerable endoscope or borescope of claim 1, wherein the central passages of said flat washers are generally cruciform with a ring of said washer having four inwardly directed lobes disposed at ninety-degree intervals, and wherein said bores are disposed in said lobes.

5. The steerable endoscope or borescope of claim 1, wherein said washers are composed of aluminum-bronze.

6. The steerable endoscope or borescope of claim 1, wherein said washers are composed of beryllium-copper.

7. The steerable endoscope or borescope of claim 1, wherein said washers have a predetermined thickness, and said beads define a predetermined spacing between successive washers, and said thickness and said spacing are selected in a ratio of about 0.5:1 to 2.5:1.

8. The steerable endoscope or borescope of claim 1, further comprising an additional bead interposed between at least one pair of said hemispherical beads.

9. A steerable endoscope or borescope of the type having a viewing head and a cable-bendable steering section disposed proximally of said viewing head including a flexible sheath, a plurality of washers each having a central passage and at least one pair of peripheral bores, said bores of each pair being disposed diametrically opposite each other, and said washers being stacked with said bores generally in registry with one another; at least one pair of steering cables, each cable passing through aligned respective bores of said washers, and pairs of pivot spacer means disposed between at least certain successive ones of said washers defining bending locations for bending the steering section in one plane when one pair of said steering cables is displaced; and tuning spacer means disposed in selected spaes between said certain ones of said washers at the location of one of said bores only, in addition to the associated pivot spacer means, such that said steering section is limited more in its bending in one direction than in the opposite direction in said one plane.

10. The steerable endoscope or borescope of claim 9, wherein there are two paris of said steering cables and two said pairs of bores in said washers, wherein said pivot spacer means are disposed alternately at one said pair of bores and then at the other said pair of bores for successive ones of said washers, and said tuning spacer means are disposed at the location of one of the bores not occupied by the associated pivot spacer means.

11. The steerable endoscope or borescope of claim 9, wherein said tuning spacer means are disposed at alternate spaces between washers in sequence beginning at the proximal end of the steering section.

12. The steerable endoscope or borescope of claim 9, wherein said tuning spacer means are disposed so as to limit the turning in said one direction to about 90 degrees.

13. The steerable endoscope or borescope of claim 9, wherein said tuning spacer means include spacer beads disposed on said steering cables between selected ones of said washers.

14. The steerable endoscope or borescope of claim 9, wherein there are two pairs of said steering cables and two said pairs of bores in said washers, and further comprising tuning spacer means disposed at the locations of one only of the other pair of said peripheral bores disposed in said alternate spaces between said washers to limit bending of the steering section in said other plane in the direction of the tuning spacer means.

15. The steerable endoscope or borescope of claim 9, wherein at least two successive said washers near he proximal end of said steering section are provided without said spacer means therebetween.

* * * * *